United States Patent [19]
Laugier et al.

[11] Patent Number: 5,814,305
[45] Date of Patent: Sep. 29, 1998

[54] USE OF HYDROPHILIC PENETRATION AGENTS IN DERMATOLOGICAL COMPOSITIONS FOR THE TREATMENT OF ONYCHOMYCOSES, AND CORRESPONDING COMPOSITIONS

[75] Inventors: Jean-Pierre Laugier, Antony; Marie-France Rude, Villejuif; Philippe Touzan, Ramonville Saint Agne; François Rigenbach, Bagneux, all of France

[73] Assignee: Novartis AG, Basel, Switzerland

[21] Appl. No.: 381,583

[22] Filed: Jan. 30, 1995

Related U.S. Application Data

[63] Continuation of Ser. No. 101,722, Aug. 4, 1993, abandoned, which is a continuation of Ser. No. 846,613, Mar. 5, 1992, abandoned.

[30] Foreign Application Priority Data

Mar. 8, 1991 [FR] France ................................ 91 02838

[51] Int. Cl.$^6$ ............................ H61K 7/04; H61K 7/043
[52] U.S. Cl. ............................ 424/61; 514/858; 514/947
[58] Field of Search ............................ 424/61; 514/858, 514/947

[56] References Cited

U.S. PATENT DOCUMENTS

| | | | |
|---|---|---|---|
| 4,470,962 | 9/1984 | Keith et al. | 424/28 |
| 4,859,696 | 8/1989 | Kamiya et al. | 514/420 |
| 4,886,545 | 12/1989 | Peck et al. | 71/88 |
| 4,920,112 | 4/1990 | Onishi et al. | 514/171 |
| 4,946,870 | 8/1990 | Partain, III et al. | 514/777 |
| 5,053,227 | 10/1991 | Chiang et al. | 424/448 |
| 5,181,914 | 1/1993 | Zook | 604/307 |
| 5,215,520 | 6/1993 | Shroot et al. | 604/20 |
| 5,256,647 | 10/1993 | Minaskanian et al. | 514/24 |
| 5,264,206 | 11/1993 | Bohn et al. | 424/61 |

FOREIGN PATENT DOCUMENTS

| | | |
|---|---|---|
| 5459590 | 11/1990 | Australia. |
| 2098865 | 4/1982 | United Kingdom. |
| 2197194 | 5/1988 | United Kingdom. |
| 8702580 | 5/1987 | WIPO. |

*Primary Examiner*—Sally Gardner-Lane
*Attorney, Agent, or Firm*—Carol A. Loeschorn

[57] ABSTRACT

The hydrophilic penetration agents customarily used for the transcutaneous penetration of active ingredients are, surprisingly, found to improve the penetration of antifungal agents through the nails. A corresponding dermatological composition contains at least one antifungal agent chosen, in particular, from among those of the allylamine family, such as terbinafine-HCl and naftifine-HCl; at least one hydrophilic penetration agent chosen, in particular, from among the glycols, glycol monoethers, glycol diethers, dimethylsulphoxide, caprolactam, dimethylisosorbide, isopropylidene glycerol, dimethylimidazolidinone, ethyl lactate, the polyoxyethylenated $C_8$–$C_{10}$ glycerides, polyethylene glycol 20 glyceryl laurate and dimethylacetamide; and a water-alcohol solvent medium which dissolves the said antifungal agent(s) and in which the said penetration agent (s) is (or are) at least partially miscible.

11 Claims, No Drawings

USE OF HYDROPHILIC PENETRATION AGENTS IN DERMATOLOGICAL COMPOSITIONS FOR THE TREATMENT OF ONYCHOMYCOSES, AND CORRESPONDING COMPOSITIONS

This is a continuation of application Ser. No. 08/101,722, filed Aug. 4, 1993 now abandoned which in turn is a continuation of application Ser. No. 07/846,613, filed Mar. 5, 1992, now abandoned.

The present invention concerns the use of hydrophilic penetration agents in dermatological compositions for the treatment, in both man and animals, of onychomycoses mainly due to dermatophytes or Candida, and dermatological compositions containing such penetration agents.

Zaias et al. [Clinical Experimental Dermatology 1989, 14, 120–123] have described the treatment of onychomycoses due to *Trichophyton rubrum* by peroral administration of terbinafine. This antifungal agent, whose structure and activity against dermatophytic fungi are original, shows low toxicity via the oral route and can be used successfully for the long-term treatment of onychomycoses. It was found that the most effective treatment consists in the peroral administration of terbinafine 250 mg/day for 6 months. This represents an advance compared with previously known medicaments such as ketoconazole and griseofulvin. However, the administration of terbinafine shows disadvantages, namely that on the one hand the duration of the treatment is very prolonged, which carries a high risk of non-compliance, and on the other hand the cost of the treatment is extremely high, being linked to its duration and the daily assumption of terbinafine 250 mg.

For those reasons, it has long been desired to treat onychomycoses via the transungual route. The problem that then arises is to ensure that the antifungal agents will penetrate into and beneath the nail. Such antifungal agents could then advantageously consist of those belonging to the allylamine family, of which terbinafine is one, the latter being at present the only compound among the family that can be used via the oral route.

In this context, it was proposed in European Patent EP-A-0 064 830 to administer, via the transungual route, concentrated solutions of liposoluble antifungal agents belonging to the imidazole family, dissolved in fatty acids with $C_8$–$C_{20}$, such as undecylenic acid, these solutions being further solubilized in a solvent chosen from among the lower alcanols, such as ethanol and isopropanol, esters such as ethyl acetate, and ketones such as acetone and butanone-2. The $C_8$–$C_{20}$ fatty acids mentioned play the part of transungual penetration agents, while undecylenic acid also serves to potentiate the antifungal properties of the imidazoles. A composition of this type is marketed under the name "TROSYD solution", and contains 28% tioconazole; it is used to supplement oral treatments with griseofulvin.

Also known from the French patent FR-B-2 523 447, are antimycotic therapeutic preparations based on a cream or ointment containing one or more active antimycotic ingredients, together with 5–20% by weight of urea relative to the total weight of the preparation.

It is also apparent from the state of the art that, still in the attempt to increase the penetration of antifungal agents, which do not in their own right diffuse easily in the nails, compositions of the "nail varnish" type have been proposed. These contain a polymeric component and are intended to release the active agent at a programmed rate.

For example, Japanese patent JP-01-110 620 describes an antifungal composition intended for use on the nails, which contains polyvinyl acetate, an antifungal agent, preferably an imidazole, long-chain $C_8$–$C_{20}$ fatty acid esters and/or higher alcohols, and a volatile solvent.

European patent EP-A-319 964 also describes antifungal preparations of the film-forming type for external application, containing approximately 0.1–1.5% of tolnaftate, about 10–20% of a methacrylate copolymer of dimethylaminoethyl methacrylic acid ester, and about 0.5–10% of a medium-chain fatty acid ester, in an alcohol solvent containing almost no water. The tolnaftate is released progressively from the polymeric matrix and penetration is favoured by the fatty acid ester in an anhydrous medium.

In addition, German patent DE-A-3 544 983 describes antimycotic nail varnishes containing a film-former insoluble in water, an antifungal agent from the hydroxy-1-pyridone-2 series, such as cyclopirox or octopirox, and an exclusively anhydrous solvent.

International patent application WO 87/02580 discloses a pharmaceutical vehicle capable of supplying an active ingredient to the nails. This consists of a hydrophilic polymer and a pharmaceutically acceptable solvent for the hydrophilic polymer. Example 2 mentions the association of an antifungal agent with a hydrophilic polymer, in a vehicle based on ethanol and water. The antifungal agent should preferably have a molecular weight lower than 300 and a solubility in water of at least 0.01% by weight.

German patent application DE-A-3 720 147 also discloses varnishes for the treatment of onychomycoses, containing a water-insoluble polymeric film-former, an antifungal substance of the imidazole type, tolnaftate, naftifine hydrochloride, and a solvent for the film-forming polymer chosen from among the organic solvents commonly used in the field of cosmetics to manufacture nail varnishes, with a low boiling point of less than 100° C. Example 8 of that patent application concerns a varnish containing an antifungal agent of the allylamine family (naftifine hydrochloride), 4% of water, polyvinylbutyrate as the film-forming polymer, nitrocellulose and ethyl acetate.

Thus, the state of the art comprises compositions based on a low-molecular-weight antifungal agent, in a water-alcohol mixture in which the said antifungal agent can be dissolved, to which is added a hydrophilic polymer as in the case of international patent application WO 47/02580, or a water-insoluble polymer as in the case of patent application DE-A-3 720 147. However, none of these compositions gives really good results. Formulations such as those described in example 8 of German patent application DE-A-3 720 147 have a number of disadvantages which do not allow the desired results to be achieved in the treatment of onychomycoses:

in the first place, the polymers used hinder the release of the active ingredient: when the solvents have evaporated, the polymer network retains the naftifine and hinders its penetration into the stratum corneum;

during a second application, there is an accumulation of the couple polymer+active ingredient at the surface of the first layer, which accounts for the non-penetration of the active ingredient;

nitrocellulose is a powerful oxidizing agent and naftifine is chemically unstable in this medium, and is therefore rendered inactive; and ethyl acetate is well known to dehydrate the nails and so slow down the penetration of the antifungal agent; in effect, it is a lipophilic solvent which counteracts the desired effect.

In searching for a solution to the problem posed, it was discovered that the hydrophilic penetration agents used to promote the transcutaneous penetration of active ingredients possess the property of considerably increasing the concentration of antifungal agent in and beneath the nail.

This result is completely unexpected, because numerous scientific studies have demonstrated that nails are hydrophilic in character, i.e. they behave as a hydrogel in contrast to the stratum corneum of the skin, which is lipophilic and behaves as a water barrier. Because of this, it is surprising that the penetration agents currently used to pass through the stratum corneum favour the penetration of antifungal agents into the nails, as shown in example 10 below.

The first aim of the present invention is thus to use hydrophilic penetration agents of the type usually used for the transcutaneous penetration of active ingredients, to improve the penetration of antifungal agents through the nails, in dermatological compositions intended for the treatment of onychomycoses.

The present invention also concerns a dermatological composition intended for the treatment of onychomycoses, presented in the form of a solution and containing, on the one hand, an effective quantity of at least one antifungal agent, and on the other hand, an effective quantity of at least one agent that favours the penetration of the said antifungal agent(s) into and through the keratinized ungual layer of the nail, and finally a solvent medium for the said antifungal agent(s), characterized in that the said antifungal agent(s) is (or are) at least partially soluble in water, that the said solvent medium contains water mixed with at least one co-solvent chosen from among the $C_2$–$C_8$ alcanols with straight or branched chains, and that the said penetration agent(s) is (or are) hydrophilic and at least partially miscible with the said solvent medium.

The preferred antifungal agents are those belonging to the allylamine family. Terbinafine hydrochloride and naftifine hydrochloride may be mentioned in particular; their respective formulae are as follows:

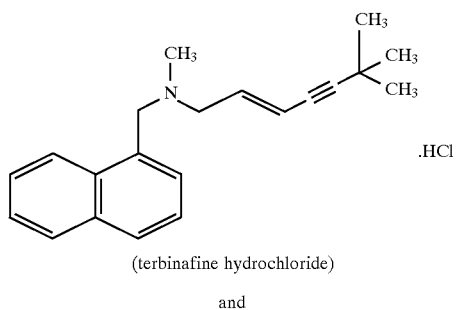

(terbinafine hydrochloride)

and

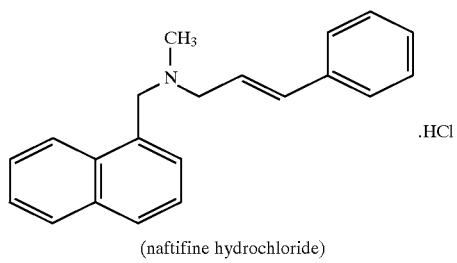

(naftifine hydrochloride)

The antifungal agent concentration is approximately 2 to 30% by weight, preferably 5 to 20% by weight, relative to the total weight of the composition.

The hydrophilic penetration agents may advantageously be chosen from among the following:

the glycols, for example propylene glycol, butylene glycol, hexylene glycol, ethylene glycol and the polyethylene glycols;

the glycol monoethers, for example the ethylene glycol monoethers marketed under the names "DOWANOL PM, DPM, TPM, PnB, PPH, DPnB, TPnB, PMA";

the glycol diethers, for example those marketed under the name of "PROGLYDES®", in particular propylene glycol dimethyl ether and dipropylene glycol dimethyl ether;

dimethylsulphoxide, caprolactam, dimethylisosorbide, isopropylidene glycerol, dimethylimidazolidinone, N-methyl-pyrrolidone-2, pyrrolidone-2, ethyl lactate, the polyoxyethylenated $C_8$–$C_{10}$, glycerides, notably those marketed under the name "LABRASOL®", polyethylene glycol 20 glyceryl laurate, and dimethylacetamide.

The concentration of penetration agent(s) may advantageously range from about 1 to 60% by weight, relative to the total weight of the composition.

The solvent medium may advantageously consist of water mixed with at least one co-solvent chosen from among the group comprising the C2–C8 alcanols with straight or branched chains. For the co-solvent, ethanol, isopropanol and n-butanol may be mentioned as preferable.

Water is present in a proportion of 5 to 30% by weight relative to the total weight; as for the concentration of the co-solvent(s), this can range from 10 to 90% by weight, relative to the total weight of the said composition.

For preference, the composition conforming to the invention is free from any surfactant; however, it may contain at least one additive chosen from among the group consisting of preservative agents, such as phenylethyl alcohol, benzyl alcohol and phenoxyethanol; antioxidants such as butylhydroxyanisole-(BHA), butylhydroxytoluene (BHT), palmityl ascorbate, α-tocopherol and/or its esters; colorants, charges or pigments, such as the micatitans currently used in the cosmetic field for the manufacture of nail varnishes; and polymers capable of preventing the running of the composition before penetration, for example alkylcellulose derivatives that are totally soluble in the solvent medium used and chosen, in particular, from among the methylcelluloses, ethylcelluloses and hydroxyalkylcelluloses, such as those marketed under the name "KLUCEL".

The composition conforming to the invention may advantageously be presented in the form of a lotion or a fluid gel.

For a better understanding of the object of the invention, several versions of it will now be described. These are intended as purely illustrative examples with no limitative implications:

EXAMPLE 1

The following formulation is prepared:

| Terbinafine-HCl | 10% by weight |
| Ethanol | 30% |
| Purified water | 30% |
| Diethylene glycol monoethyl ether | 30% |

The terbinafine-HCl is dissolved in the water-alcohol mixture at 30° C. with stirring, and the diethylene glycol monoethyl ether is then added progressively until fully dissolved. The lotion so obtained is applied to the diseased nails for the purpose of treating an onychomycosis, using either a small brush or a pump-action spray.

An improvement in the condition of the nail becomes apparent from the second month of the treatment. This takes the form of the growth of healthy nail, which progressively eliminates the diseased nail.

In each of the examples 2 to 8 that follow, the procedure described in example 1 is repeated, to obtain a lotion which is applied as in example 1; in example 9, a gel is obtained but the method of application stays the same. A significant improvement of the onychomycosis is observed in the second month of the treatment. All the concentrations are given in percentage by weight relative to the total weight of the composition.

EXAMPLE 2

The following composition is prepared:

| | |
|---|---|
| Terbinafine-HCl | 15% |
| Isopropanol | 40% |
| Purified water | 20% |
| Propylene glycol monomethyl ether | 25% |

EXAMPLE 3

The following composition is prepared:

| | |
|---|---|
| Terbinafine-HCl | 5% |
| n-butanol | 75% |
| Tripropylene glycol monomethyl ether | 5% |
| Purified water | 15% |

EXAMPLE 4

The following composition is prepared:

| | |
|---|---|
| Naftifine-HCl | 10% |
| Ethanol | 64% |
| Purified water | 14% |
| Dimethylisosorbide | 12% |

EXAMPLE 5

The following composition is prepared:

| | |
|---|---|
| Naftifine-HCl | 10% |
| Isopropanol | 30% |
| Purified water | 30% |
| Isopropylidene glycerol marketed under the name "SOLKETAL" | 30% |

EXAMPLE 6

The following composition is prepared;

| | |
|---|---|
| Naftifine-HCl | 5% |
| Isopropanol | 35% |
| Purified Water | 30% |
| Caprolactam | 30% |

EXAMPLE 7

The following composition is prepared:

| | |
|---|---|
| Terbinafine-HCl | 5% |
| Purified Water | 15% |
| Ethanol | 56.8% |
| Dimethylsulphoxide | 15% |
| Polyethylene glycol 20 glyceryl laurate | 8% |
| Butylhydroxytoluene | 0.1% |
| Butylhydroxyanisole | 0.1% |

EXAMPLE 8

The following composition is prepared:

| | |
|---|---|
| Terbinafine-HCl | 20% |
| Purified water | 5% |
| Ethanol | 40% |
| Tripropylene glycol mono-n-butyl ether | 5% |
| Dimethylsulphoxide | 25% |
| Dimethylimidazolidinone | 5% |

EXAMPLE 9

The following composition is prepared:

| | |
|---|---|
| Terbinafine-HCl | 8% |
| Purified water | 25% |
| Propylene glycol monomethyl ether | 30% |
| Ethanol | 36.75% |
| Butylhydroxytoluene | 0.05% |
| Hydroxypropyl cellulose | 0.2% |

EXAMPLE 10

Demonstration of the phenomenon of the penetration of an antifungal agent into the nails, thanks to a hydrophylic penetration agent.

The above penetration phenomenon was demonstrated using an in vitro model which reproduces the human nail remarkably well.

For this purpose, thin discs of horn from a bovine hoof, with a uniform thickness between 200 $\mu$m and 400 $\mu$m, are placed on the surface of Franz cells (static type). The 13 corneal layer is treated with the antifungal composition, and the "survived" liquid, beneath the lower face, is used to determine the concentration of the antifungal agent after a given time T.

Thus, when the antifungal composition to be studied is applied to the horny disc, at the end of the period T one can determine how much of the antifungal agent has remained on the surface, how much has penetrated into the horny hoof material, and how much is present in the "survived" liquid. From these findings a penetration balance can be drawn up.

In accordance with the invention a lotion of the composition indicated below was prepared (percentages by weight):

| | |
|---|---|
| Terbinafine-HCl | 10 |
| Purified water | 30 |
| Ethanol | 30 |
| Dipropylene glycol monoethyl ether | 30 |

This lotion was applied in amounts of 5 $\mu$l/cm$^2$ of horn, granted that 1 cm$^2$ of the horny material corresponded to 100 mg. At the end of 72 hours of the treatment, 0.122±0.02% (for n=11 tests) of the quantity of terbinafine-HCl applied was present within the horny material, i.e. approximately 610 ng, or about 6.10 ng of terbinafine-HCl/mg of horn material.

According to Finlay et al. (British Journal of Dermatology 1990, 123, 481–486), the concentration of terbinafine-HCl in the nails after oral treatment with 250 mg/day over a period of 8 weeks—a treatment said to have proved effective—was only 0.4±0.15 ng of terbinafine-HCl per mg of nail material. It follows that a single topical treatment for 72 hours using the lotion conforming to this invention and containing 10% of terbinafine-HCl delivers approximately 10 to 25 times more of the active ingredient than an 8-week oral treatment with 250 mg/day.

We claim:

1. A method for treating onychomycoses which comprises the step of administering a topical preparation to the nail of a subject in need of such treatment, said topical preparation comprising a pharmaceutically-effective amount of terbinafine hydrochloride and a hydrophilic penetration agent in an amount effective to allow penetration of terbinafine hydrochloride into and through the keratinized ungual layer of the nail, said hydrophilic penetration agent being selected from the group consisting of glycols, glycol monoethers, glycol diethers, dimethylsulphoxide, caprolactam, dimethylisosorbide, isopropylidene glycerol, dimethylimidazolidinone, N-methyl pyrrolidone-2, pyrrolidone-2, ethyl lactate, polyoxyethylenated $C_8$–$C_{10}$ glycerides, polyethylene glycol glyceryl laurate and dimethylacetamide.

2. A method in accordance with claim 1 wherein said terbinafine hydrochloride is present in a concentration of 2 to 30% by weight relative to the total weight of said topical preparation.

3. A method in accordance with claim 1 wherein the glycols are selected from the group consisting of propylene glycol, butylene glycol, hexylene glycol, ethylene glycol and polyethylene glycols; the glycol monoethers are selected from the group consisting of monoethers of ethylene glycol and monoethers of propylene glycol; and the glycol diethers are selected from the group consisting of propylene glycol dimethyl ether and dipropylene glycol dimethyl ether.

4. A method in accordance with claim 3 wherein said penetration agent is dipropylene glycol dimethyl ether.

5. A method in accordance with claim 1 wherein said penetration agent is present in a concentration of 1 to 60% by weight relative to the total weight of said topical preparation.

6. A method in accordance with claim 1 wherein said topical preparation further comprises water.

7. A method in accordance with claim 1 wherein said topical preparation further comprises a $C_2$–$C_8$ alkanol.

8. A method in accordance with claim 1 wherein said topical preparation further comprises at least one additive selected from the group consisting of preservative agents, antioxidants, colorants, charges, pigments and polymers intended to prevent running of the composition before penetration.

9. A method in accordance with claim 1 wherein said topical preparation is in the form of a lotion or a fluid gel.

10. A method in accordance with claim 6 wherein said water is present in an amount of 5 to 30% by weight relative to the total weight of said topical preparation.

11. A method in accordance with claim 7 wherein said $C_2$–$C_8$ alkanol is present in an amount of 10 to 90% by weight relative to the total weight of said topical preparation.

* * * * *